United States Patent [19]

Prosen

[11] 4,263,045

[45] Apr. 21, 1981

[54] STAINLESS DENTAL ALLOY FOR APPLICATION OF LOW-FUSING OPAQUEING PORCELAIN

[75] Inventor: Emil M. Prosen, Bala-Cynwyd, Pa.

[73] Assignee: Neoloy Products, Inc., Posen, Ill.

[21] Appl. No.: 71,128

[22] Filed: Aug. 30, 1979

[51] Int. Cl.$^3$ ............................................. C22C 19/07
[52] U.S. Cl. ..................................... 75/134 C; 75/171
[58] Field of Search .................. 75/171, 134 C, 134 F

[56] References Cited

U.S. PATENT DOCUMENTS 2,570,355  10/1951  Low ........................................ 75/171

*Primary Examiner*—R. Dean
*Attorney, Agent, or Firm*—Jacobs & Jacobs

[57] ABSTRACT

The present invention provides a stainless dental alloy which may be used in producing crowns, bridges, inlays, and the like. It also provides an alloy which is especially adapted for the application of low-fusing opaqueing porcelain for adhesion to such dental appliances. The alloy of the present invention has a melting point approximating 2650° F. In its broadest aspect the alloy consists of cobalt 40 to 60%, chromium 18 to 35%, tungsten 5 to 20%, molybdenum 1 to 4%, copper 0.5 to 2%, iron 1 to 3%, manganese 0.5 to 2%, niobium 0.5 to 2%, and silicon 0.25 to 1%.

4 Claims, No Drawings

STAINLESS DENTAL ALLOY FOR APPLICATION OF LOW-FUSING OPAQUEING PORCELAIN

The present invention relates to a stainless dental alloy especially adapted for use in the dental field for the preparation of crowns, bridges, inlays, and other dental prostheses to which it is desired to apply a porcelain surface. The principal advantage of the alloy of the present invention is that it provides an alloy to which a low-fusing porcelain can be adhered by fusion, with none of the disadvantages of heretofore known alloys.

It is also an economy alloy in that it does not contain any of the higher priced precious metals such as gold and platinum.

BACKGROUND OF THE INVENTION

In the dental field it is now well recognized that the alloy to which low-fusing porcelain can be successfully applied so as to have complete adhesion must be compatible from the standpoint of coefficient of linear expansion and contraction at the fusing temperature of the porcelain; and that such alloy must provide on its surface oxides which facilitate the adhesion of the porcelain. Furthermore, the oxides have to be an integral part of the alloy, so that such oxides cannot be lifted from the alloy by the fluxing effect during the application of opaque porcelain to the alloy.

It is also well understood that after application of the porcelain to the alloy, the porcelain surface should not check, crack or separate from the base alloy.

There are on the market today various opaque porcelains which are especially prepared and sold for application to dental alloys. The opaqueing materials of such opaque porcelains vary from one to the other and the basic ingredients of such opaque porcelains are not fully disclosed in any literature with which I am familiar.

Among the various opaqueing porcelains with which I am familiar is one offered for sale and sold by Dentsply International Inc. of York, Pennsylvania under the trademark BIOBOND. Another is offered and sold by Vita Zahnfabrik H. Rauter K.G., of Sackingen, Germany, under the trademark VITA.

I also know that there are other opaque porcelains sold under the trademark CERAMCO by Ceramco, Inc. of Long Island City, New York and under the trademark HOWMEDICA by Howmedica, Inc. of New York, New York.

Essentially all of these opaque porcelains for dental application are said to be low fusing in that they will fuse at a temperature of about 1800° F. to dental alloys and will adhere to the same provided all other conditions are met for fusing such porcelains to the metal alloy.

SUMMARY OF THE INVENTION

According to the present invention, and after considerable experimental work, I have found that a stainless alloy consisting of the following elements in its preferred form can be fused to BIOBOND, VITA, CERAMCO and HOWMEDICA opaque porcelains with excellent results. The preferred formulation for such an alloy is:

Cobalt 56%
Chromium 28%
Tungsten 10%
Molybdenum 2%
Copper 1%
Iron 1%
Manganese 0.80%
Niobium 0.70%
Silicon 0.50%

According to tests which I have conducted, I can state that an alloy of this preferred formulation has the following mechanical characteristics:

Melting Point 2650° F.
Thermal coefficient of expansion $1.4 \times 10^{-5}$ per °C.

DESCRIPTION OF THE INVENTION

Supplementing what is set forth under the foregoing heading of "Summary of The Invention", I have found that an alloy prepared according to the preferred formulation set forth, is ideally suited for fusing at approximately 1800° F. with opaque porcelains such as BIOBOND, VITA, CERAMCO and HOWMEDICA. The first coating of opaque porcelain is fused to the alloy at 10° F. above the recommended temperature of approximately 1800° F., in order to achieve the tenacious union between the oxides of the alloy and the opaque porcelain. The second coating of the opaque porcelain may be applied at the recommended temperature of approximately 1800° F. After fusing and cooling, such porcelains are so adherent to the alloy that it is impossible to separate the same under repeated hammer blows.

It is my firm belief from considerable experimental work in this area that the elements molybdenum, niobium, copper, manganese and iron, which are only added in small quantities to the basic alloy of cobalt, chromium and tungsten, contribute totally to the porcelain adhesive characteristics imparted to the alloy, and that without such additives insufficient oxides would be formed on the surface of such alloy. The small amounts of these elements form oxides which resist lifting of the porcelain from the alloy during fluxing of the porcelain. Molybdenum, copper and niobium in the small quantities recommended contribute most in providing the tenacious oxides for adherence of the opaque porcelain.

In my copending application Ser. No. 51,003, filed June 22, 1979, I have disclosed a non-precious stainless dental alloy having a melting temperature of 2550° F. which is especially adapted for bonding to opaqueing porcelains such as BIOBOND and VITA mentioned above. According to the present invention, I have found that the present alloy which melts at 2650° F. is especially adapted for bonding to all opaque porcelains, such as BIOBOND, VITA, CERAMCO and HOWMEDICA, as identified above.

From my experimentation I have found that the alloy of my copending application which contains niobium and gallium in small quantities and which melts at approximately 2250° F., is ideally suited for fusion to BIOBOND and VITA opaque porcelains; whereas the alloy of the present invention which contains no gallium but instead contains molybdenum, copper and niobium in small quantities, is ideally suited for fusion to all opaque porcelains.

In the broader aspect of the invention, I have found that the various elements constituting the alloy of the present invention may vary within the following ranges:

Cobalt 40 to 60%
Chromium 18 to 35%
Tungsten 5 to 20%
Molybdenum 1 to 4%
Copper 0.5 to 2%

Iron 1 to 3%
Manganese 0.5 to 2%
Niobium 0.5 to 2%
Silicon 0.25 to 1%

Within these ranges the three principal elements of cobalt, chromium and tungsten must be so proportioned as to assure that the coefficient of expansion and contraction of the alloy is suitable for porcelain application. Such coefficient of expansion must be approximately $1.4 \times 10^{-5}$ per °C. It can be slightly higher or slightly lower. The desired coefficient of expansion is accomplished by increasing the amount of chromium and tungsten and reducing the amount of cobalt.

It should also be noted that the amounts of molybdenum, copper, niobium, manganese and iron, which chiefly provide the oxides for porcelain application, are limited to very minor ranges. Of these elements, molybdenum, copper and niobium perform the same functions as niobium and gallium in my earlier application Ser. No. 51,003.

What I claim is:

1. A dental alloy especially adapted for the adhesion of opaqueing porcelain having a fusing temperature of approximately 1800° F., consisting essentially of:
   Cobalt 40 to 60%
   Chromium 18 to 35%
   Tungsten 5 to 20%
   Molybdenum 1 to 4%
   Copper 0.5 to 2%
   Iron 1 to 3%
   Manganese 0.5 to 2%
   Niobium 0.5 to 2%
   Silicon 0.25 to 1% said alloy having a melting temperature of approximately 2650° F., and a linear coefficient of expansion of about $1.4 \times 10^{-5}$ per °C.

2. A dental alloy according to claim 1, wherein the percentages of cobalt, chromium and tungsten are varied within the limits set forth to produce the melting temperature of approximately 2650° F.

3. A dental alloy consisting essentially of:
   Cobalt 56%
   Chromium 28%
   Tungsten 10%
   Molybdenum 2%
   Copper 1%
   Iron 1%
   Manganese 0.80%
   Niobium 0.70%
   Silicon 0.50%

4. A dental alloy according to claim 3, especially adapted for adhesion to opaqueing porcelain having a fusing temperature of approximately 1800° F., said dental alloy having a melting temperature of approximately 2650° F. and a linear coefficient of expansion of approximately $1.4 \times 10^{-5}$ per °C.

* * * * *